United States Patent [19]

Boltze et al.

[11] 4,104,278

[45] Aug. 1, 1978

[54] PROCESS FOR THE PRODUCTION OF COMPOUNDS WITH ANTIPHLOGISTIC ACTIVITY

[75] Inventors: Karl-Heinz Boltze, Bensberg-Kippekausen; Otfried Brendler, Cologne (Mülheim); Peter-Rudolf Seidel, Porz-Wahnheide, all of Germany

[73] Assignee: Troponwerke Dinklage & Co., Cologne (Mülheim), Germany

[21] Appl. No.: 639,674

[22] Filed: Dec. 11, 1975

Related U.S. Application Data

[63] Continuation of Ser. No. 413,135, Nov. 5, 1973, abandoned.

[30] Foreign Application Priority Data

Nov. 25, 1972 [DE] Fed. Rep. of Germany ....... 2257867

[51] Int. Cl.² ............................................. C07D 209/18
[52] U.S. Cl. ............................................. 260/326.13 A
[58] Field of Search ............................... 260/326.13 A

[56] References Cited

U.S. PATENT DOCUMENTS

| | | | |
|---|---|---|---|
| 3,390,154 | 6/1968 | Gal | 260/326.13 A |
| 3,483,220 | 12/1969 | Gaines et al. | 260/326.13 A |
| 3,919,247 | 11/1975 | Pakula et al. | 260/326.13 A X |

*Primary Examiner*—Ethel G. Love
*Attorney, Agent, or Firm*—Burgess, Dinklage & Sprung

[57] ABSTRACT

Process for the production of a compound of the formula

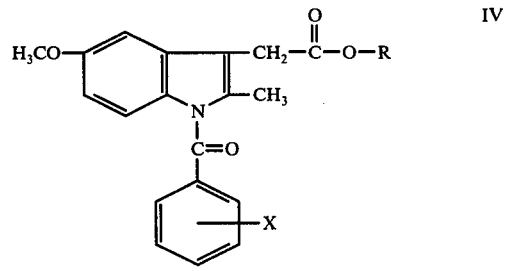

in which R stands for a benzyl radical or the radical

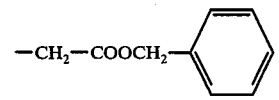

and X is hydrogen or represents one or more substituents, wherein a compound of the formula

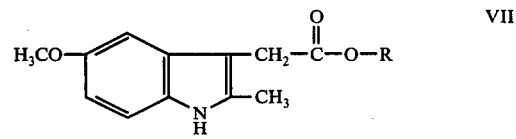

is condensed with a compound of the formula

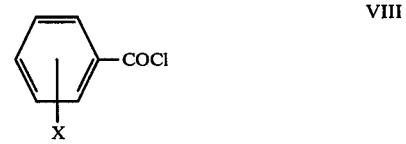

in which R and X have the meaning indicated, at temperatures of at least 100° C on an inert solvent as reaction medium, with formation of free HCl. The products are useful as intermediates for production of the corresponding indole derivatives wherein R is replaced by hydrogen or —CH₂COOH, which are antiphlogistically active compounds.

13 Claims, No Drawings

PROCESS FOR THE PRODUCTION OF COMPOUNDS WITH ANTIPHLOGISTIC ACTIVITY

This is a continuation of application Ser. No. 413,135, filed Nov. 5, 1973, now abandoned.

The present invention relates to a new, chemically original process for the production of products which can be used for the synthesis of antiphlogistically active compounds of the general formula

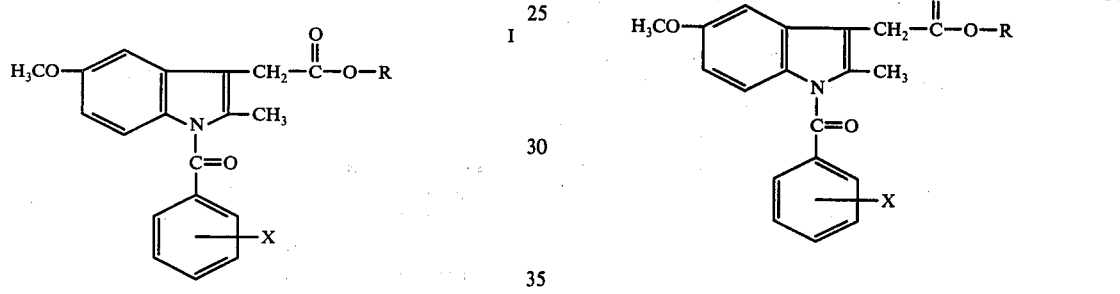

in which R stands for a hydrogen atom or for a —CH$_2$—COOH group and X is hydrogen or represents one or more halogen atoms or functional groups, such as methoxy, nitro or trifluormethyl groups. In particular it is concerned with 1-(p-chlorobenzoyl)-5-methoxy-2-methyl-3-indole acetic acid

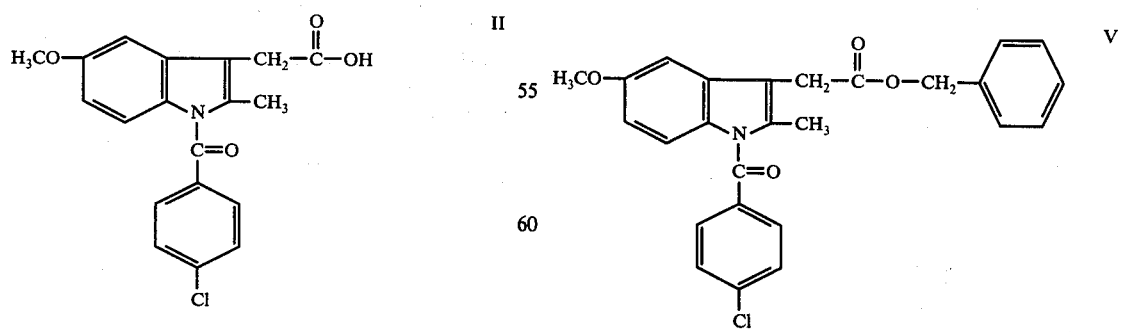

and 2-[1-(p-chlorobenzoyl)-5-methoxy-2-methyl-3-indole]-acetoxy acetic acid

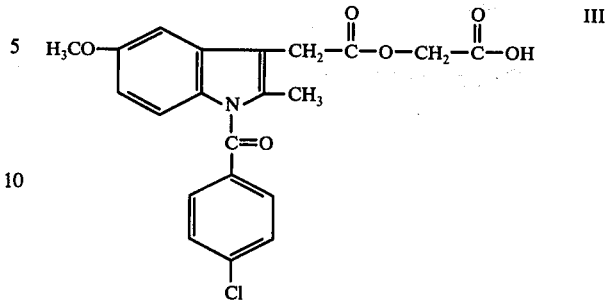

As regards the intermediate products produced by the process of the invention, these are compounds of the general formula

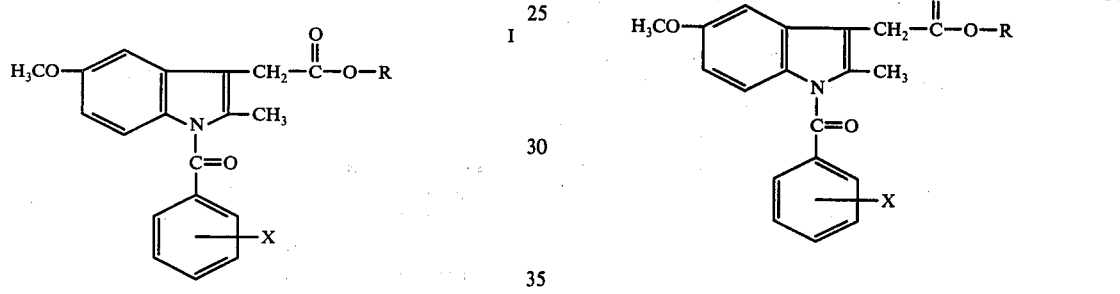

in which R stands for a benzyl radical or the radical

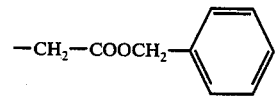

and X has the meaning indicated above, more particularly the compounds 1-(p-chlorobenzoyl)-5-methoxy-2-methyl-3-indole benzyl acetate

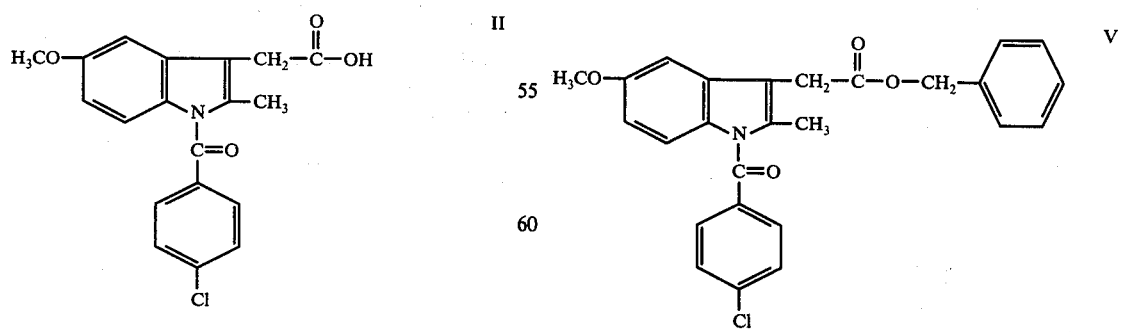

and 2-[1-(p-chlorobenzoyl)-5-methoxy-2-methyl-3-indole]-benzylacetoxy acetate

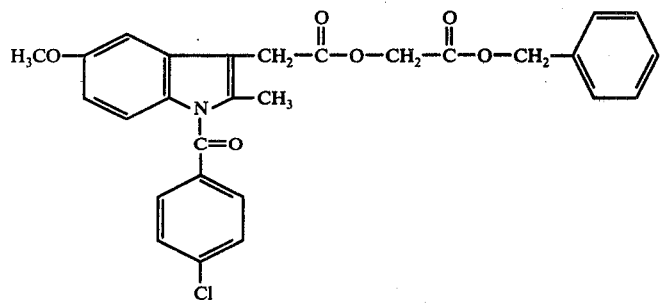

VI

It is already known to produce the compounds of the general formula I, more particularly the compound II, by condensing p-methoxyphenyl hydrazine with levulinic acid to 5-methoxy-2-methyl-3-indole acetic acid, followed by acylation with the halides, the azide or the anhydride of p-chlorobenzoic acid in the presence of sodium hydride (see German Auslegeschrift No. 1,620,030). The synthesis is effected in accordance with the following reaction diagram

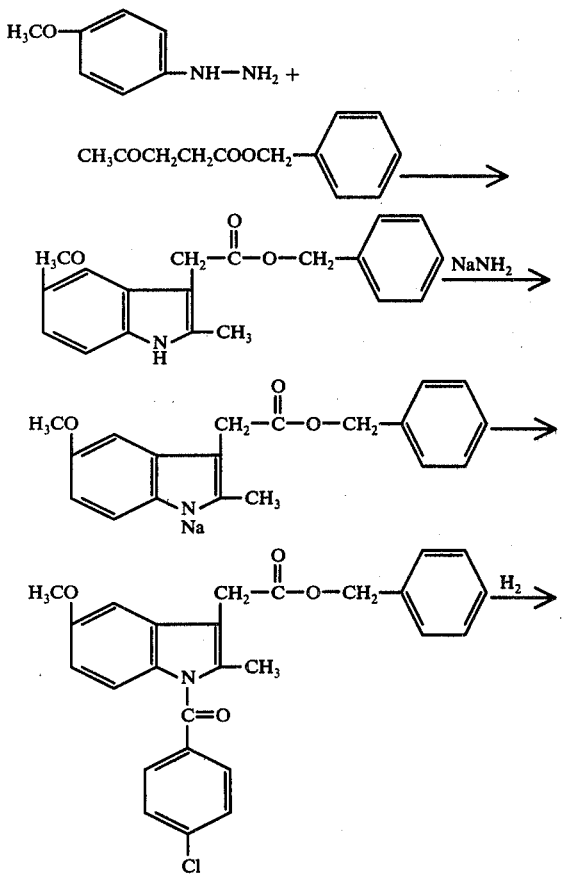

-continued

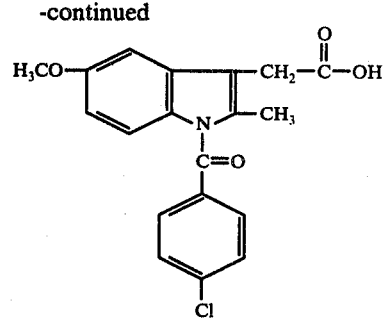

The acylation of the indole compound has however proved to be difficult (see German Offenlegungsschrift No. 1,670,001, page 2, para. 2) and the acylation is very involved and generally provides poor yields (German Offenlegungsschrift No. 1,770,157, page 2, first paragraph). The use of the free acid or normal ester, as for example the methyl ester, is excluded, since in the former case the free acid is likewise converted into the anhydride, with the splitting of which the N-acylation is cancelled out, while in the latter case the methyl ester has to be hydrolysed, in which case also N-deacylation occurs. Consequently, the tertiary butyl ester has been proposed as an ester grouping which can be easily split off. However, as indicated in German Offenlegungsschrift No. 1,770,157 (page 2, last paragraph, and page 3), this ester can only be produced with extreme difficulty and is unsuitable for technical synthesis. As one way out, it has consequently been proposed in German Offenlegungsschrift No. 1,793,678 that p-methoxyphenol hydrazine used as starting compound should be first of all acylated on the $N_{(1)}$ position and thereafter the condensation should be carried out with levulinic acid. This process does indeed lead to satisfactory yields, but is complicated insofar as the $N_{(2)}$ group initially has to be protected before the acylation and thereafter this protective group has to be removed after the acylation. The synthesis is effected in accordance with the following diagram:

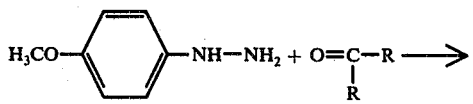

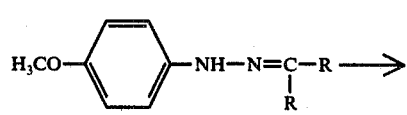

-continued

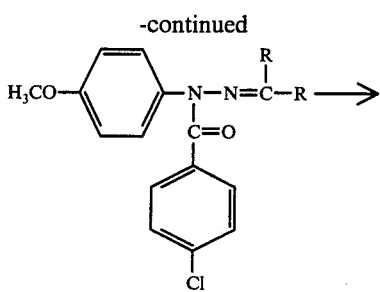

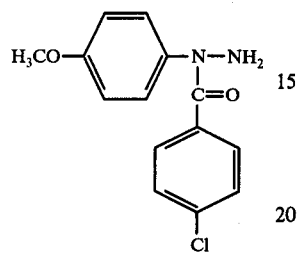

Attempts have also been made to carry out the acylation of the indole compounds with particularly reactive acylation agents. It has for example been proposed to use p-chlorobenzoyl cyanide in the presence of amines as catalyst. This compound can only be used on an industrial scale if costly precautionary measures are observed since it decomposes already at room temperature to benzoic acid and hydrogen cyanide in the presence of traces of moisture. It is only the use of readily decomposable, very reactive mixed anhydrides, e.g. the anhydride between p-chlorobenzoic acid and monoethyl carbonate

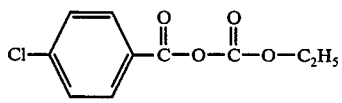

(see German Pat. No. 1,693,001) which leads to better yields of acylated indoles in the presence of catalytic quantities of amines, e.g. of triethylamine. However, this method has some disadvantages. In the first place, highly contaminated products are frequently formed, the purification of which is only possible by chromatography, that is, a method which can only be carried out with difficulty on an industrial scale. Secondly, the class of compounds has little stability and considerable decompositions already occurs at temperatures at which a noticeable N-acylation still does not take place. As decomposition products the ethylbenzoates, which are no longer suitable for acylation, and benzanhydride were found (see J. Org. Chem. 24 (1959), page 775, reaction equation). The latter is however only conditionally suitable as acylation agent in this case, since it is known from German Offenlegungsschrift No. 1,695,484 that, with the acylation of indole compounds with p-chlorobenzanhydride in the presence of catalytic quantities of camphor-sulphonic acid, the acylation is only effected to a yield of 5% (see page 6). Some experiments for obtaining a better yield with the aid of acid catalysts, as for example hydrogen bromide, trifluomethyl sulphonic acid, aluminum chloride or boron trifluoride, were unsuccessful.

The invention starts from the surprising discovery that an immediate N-acylation of indole substances can be carried out with high yields and above-average purity if the readily available corresponding benzoyl chloride is heated in inert solvents with the indole substance containing the —NH-group at relatively high temperatures. This reaction proceeds in a particularly advantageous manner when working in the absence of oxygen. It was above all not to be expected that the hydrogen chloride itself, being liberated in the reaction, does not attack the indole compounds at temperatures up to and also above 200° C, as is the case for example with all other acid catalysts as previously mentioned.

The subject of the invention is consequently a new and chemically original process for the production of compounds of the general formula IV, and in particular of V and VI, which is characterised in that compounds of the general formula VII

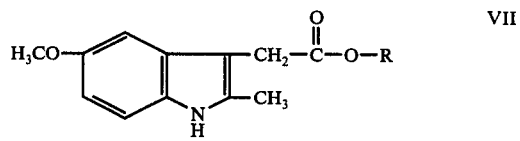

in which R represents the benzyl radical or the radical

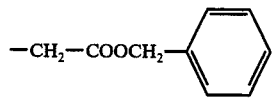

are condensed with compounds of the general formula VIII

in which X is hydrogen or also stands for one or more halogen atoms or functional groups, such as methoxy, nitro or trifluomethyl groups, at temperatures of at least 100° C, in inert solvents with formation of free HCl.

The compounds of the general formula VII used as starting substances are known. More particularly to be mentioned as starting materials of the general formula VIII are benzoyl chloride, p-chlorobenzoyl chloride, 3,4,5-trimethoxybenzoyl chloride and 4-chloro-3-nitrobenzoyl chloride.

Inert solvents are those solvents which boil above 100° C and, at these temperatures, do not react with the reaction components, more particularly the compounds of the general formula VII. These include aromatic hydrocarbons such as toluene, ethylbenzene, isopropylbenzene, butylbenzene, diethylbenzene, xylene, 1,2,4-trimethylbenzene, 1,3,5-trimethylbenzene, 1,2,3,4-tetrahydronaphthalene, 1-methyl-4-isopropylbenzene and decalin. Also to be mentioned are aliphatic hydrocarbons, such as nonane, decane, decaline, undecane, dodecane and bicyclohexyl. Especially suitable are hydrocarbon mixtures, such as kerosene, paraffin oil, isoparaffins, but more particularly the so-called white spirits (b.p. 180°–210° C) and special petroleum (b.p. 180°–220° C). Very suitable for the reaction are also a series of chlorinated hydrocarbons, such as chlorobenzene 1,2-dichlorobenzene, 1,3-dichlorobenzene, 1,1,2,2-tetrachlorethane, 2-chloro-, 2,4-dichloro- and 3,4- dichlorotoluene. Aliphatic and aromatic ethers, such as diglym, diethyleneglycol diether, anisol, phenetol, diphenylether and veratrol are also suitable. Finally, also other hydrocarbons with oxygen functions, e.g. diisobutylketone, can be used as solvents. Particularly preferred are those solvents which boil between 170° and 220° C, advantageously between 180° and 205° C.

The process according to the invention proceeds in accordance with the reaction diagram.

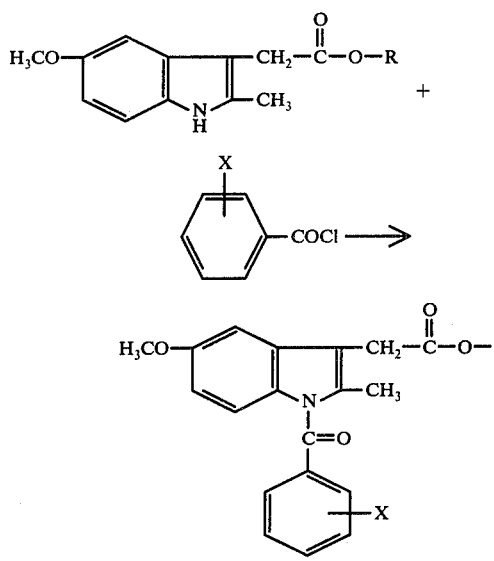

The hydrogen chloride being liberated during the reaction may, by titrimetric determination, be used as a standard for the progress of the reaction.

The conversion is advantageously effected at temperatures between 100° and 220° C, more particularly between 170° and 210° C. The reaction period depends on the nature of the solvent, its boiling point and on the concentration of the solution and usually amounts to between 3 and 24 hours. Low-boiling solvents require a longer reaction time than solvents of higher boiling point. The reaction time decreases with increasing concentration of the solution.

The end products formed of the general formula IV are of excellent purity and are obtained in particularly high yields, when the process according to the invention is carried out in the absence of oxygen, i.e. more particularly with exclusion of air.

For reliably excluding free oxygen, more especially atmospheric oxygen, it is preferred according to the invention to work in an inert gas atmosphere, i.e. under gases which themselves do not interfere chemically in the reaction. Oxygen-free nitrogen or inert gases such as helium are for example suitable for this purpose. According to the invention, it may in particular be preferred to conduct the stream of such an inert gas through the heated reaction mixture. In particular, it may also be preferred that the reactants which react with one another and/or the inert solvents introduced during the process should be flushed prior to commencement of the reaction with such a stream of inert gas, in order to ensure from the outset the absence of even traces of oxygen.

The passage of the inert gas stream through the heated reaction mixture provides the additional advantage that by this means the discharge from the reaction mixture of the free hydrohalic acid, more especially HCl, which forms with the condensation reaction is accelerated and facilitated. It was found that by this means the yield and the purity of the required end product can possibly be favourably influenced. The reaction mixture per se and consequently more particularly the indole starting compound is astonishingly stable with respect to dry oxygen-free HCl, also at the said high reaction temperatures. Thus, it was established by tests that, with suitable solvents, even with passage of gaseous, dry HCl for several hours through a reaction batch, no appreciable resinification of the indole compound occurs, if this treatment is effected in the absence of the acylating acid chloride. The dry, gaseous HCl liberated by reaction of the acid chloride in the condensation reaction according to the invention therefore leads to a surprisingly small degree to undesirable secondary reactions. This was all the more surprising, in that the addition of any other strong acids immediately leads to the rapid resinification of substantial quantities of the reaction mixture. The same applies as regards the concurrent use of acid catalysts of the Lewis acid type. Even the use of the chemically closely related acid bromide as acylation agent instead of the acid chloride, gives decidedly less satisfactory results, with formation of HBr, than the use of the acid chloride. If is from this that the particularly preferred use of the acid chloride as reaction component is derived. It is obviously indeed a particular property of the gaseous hydrochloric acid that, under the conditions indicated of the process according to the invention, it has a substantially inert behaviour with respect to the reactants. It is an interesting fact that this property is only given to the free gaseous hydrochloric acid. If one attempts to take up the hydrochloric acid in the mixture of reactants and more especially to make it harmless by formation of salt, even then there are immediate and expensive secondary reactions with resinification, if for example it is attempted to react and immediately precipitate the HCl which forms with carbonates. It is astonishing that it is just the free gaseous hydrochloric acid which is stable with respect to the reaction system according to the invention.

It is, however, preferred to keep the HCl concentration in the mixture of reactants low. This is achieved or facilitated by passing the stream of inert gas through the mixture of reactants.

It is further preferred according to the invention to exclude moisture from the reaction mixture. According to the invention, therefore, the inert gas stream is preferably in addition pre-dried. Moisture in the reaction mixture leads to the undesired reaction of the acid chloride and thus to the reduction in yield. In individual cases, it may moreover be desirable to work with exclusion of incidence of light into the reaction mixture. Nevertheless, this measure will only have particular significance in special cases.

The purity of the end products which form is a particular advantage of the process according to the invention, since when operating in accordance with the invention, end products are formed which are brought by a single crystallisation to a degree of purity which is higher than 98% and in most cases even above 99%. In principle, the reaction can of course be carried out in the presence of air and even in the absence of solvent with yields which are suitable for use. In such cases, however, there are generally obtained end products which are contaminated. It is only with extreme difficulty, if at all, that these impurities can be removed from the reaction products. Use of the process technically is therefore made considerably more difficult under these conditions.

When carrying out the process of the invention, there are preferably used 1 to 5 mols of the compounds of the general formula VIII to 1 mol of the compounds of the general formula VII. The working up of the end products is extremely simple. It is for example carried out by evaporating the diluent under vacuum, in which case, depending on solvent, either a crystal magma is already formed or the residue is caused to crystallise by adding, for example, diethylether, or the reaction solution is even diluted, for example, with diethylether, as a result of which the end products precipitate in crystalline form. These crystalline end products are thereafter recrystallised.

Finally, it is preferred with the process of the invention to use several times the amount of solvent, based on the weight of the reactants. Even if in principle the reaction takes place in the absence of solvents, it is nevertheless desirable to use at least approximately the same quantity and advantageously at least twice the quantity of the solvent, in each case based to the weight of the reactants introduced. The use of 4 to 15 times the quantity of solvent, based to the weight of reactants, can be particularly advantageous.

EXAMPLE 1

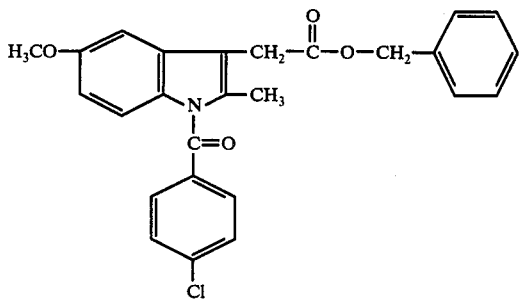

(a) 309.37 g (1 mol) of 5-methoxy-2-methyl-3-indole benzyl acetate are dissolved in 4000 ml of absolute 1,2-dichlorobenzene and heated to 160° C while passing through oxygen-free nitrogen and excluding light and moisture. Thereafter, within 15 to 20 minutes, 350 g (2 mols) of p-chlorobenzoylchloride are introduced dropwise and the reaction mixture is heated to boiling point (internal temperature 180° to 183° C). The hydrogen chloride which is liberated during the reaction is driven off with the aid of the stream of nitrogen and, for conversion control, is quantitatively determined by titration with sodium hydroxide solution. After boiling for 17 hours, the solvent and excess acid chloride are distilled off at 50° C/0.1 mm Hg, the brown oily residue is taken up in 1000 ml of diethylether and stored for 6 hours at −10° to 0° C. The solution, solidified into a mass of crystals, is filtered with suction and the residue is finally washed with isopropyl ether. The 1-(p-chlorobenzoyl)-5-methoxy-2-methyl-3-indole benzyl acetate as thus obtained is produced in a yield of 365.9 g (m.p. 95°–94° C). From the ethereal solution, another 27.3 g of this compound (m.p. 89°–90° C) crystallise out, so that the total yield is 393.2 g (=88% of the theoretical). By being recrystallised once from ethyl acetate/isopropyl ether, there is obtained a highly pure product of melting point 95°–96° C with a total yield of 83% of the theoretical.

(b) in 2000 ml of white spirit (redistilled "Kristallöl-60" of SHELL AG with a boiling range from 190°–220° C), there are suspended, while passing through oxygen-free nitrogen and with exclusion of light and moisture, 300 g (0.972 mol) of 5-methoxy-2-methyl-3-indole benzyl acetate, and subsequently the mixture is heated to 160° C (internal temperature, a clear solution being formed between 90° and 100° C) and 340 g (1.944 mols) of p-chlorobenzoyl chloride are added over a period of 15 minutes. The temperature is then raised until the solution boils (internal temperature 193°–196° C; the evolution of hydrogen chloride taking place is controlled as described under (a). After a reaction lasting 8 hours, the yellowish-brown solution is allowed to cool to 70° C and 125 ml of ethyl acetate are added at this temperature. After slow cooling and standing for a relatively long time at 0° C, the crystal magma which has formed is suction-filtered and washed with 1000 ml of isopropyl ether. The crude yield of 1-(p-chlorobenzoyl)-5-methoxy-2-methyl-3-indole benzyl acetate amounts to 396.6 g (91% of the theoretical), and after recrystallisation as described under a), the pure yield is 348.3 g (=80% of the theoretical).

(c) 300 g of 5-methoxy-2-methyl-3-indole benzyl acetate are dissolved in 2 liters of Petrol Spezial of Messrs. Fluka under heat, 350 g p-chlorobenzoyl chloride are added as described in Example 1a, and the mixture is boiled for 4 hours at 195°–198° C with introduction of argon gas. After cooling to 60° C, 2 liters of ether are added and the solution is kept in the cold. The compound worked up as in the preceding examples is obtained in a crude yield of 350 g (80% of the theoretical melting point 95°–96° C) and with a pure yield of 320 g (74% of the theoretical, melting point 96° C).

(d) 200 g (0.647 mol) of 5-methoxy-2-methyl-3-indole benzyl acetate in 1330 ml of absolute 2,4-dichlorotoluene produce, with 226 g (1.29 mols) of p-chlorobenzoyl chloride, after boiling for 4 hours at 204° C and working up as described, 232 g (80% of the theoretical) of 209 g (72% of the theoretical), respectively, of 1-(p-chlorobenzoyl)-5-methoxy-2-methyl-3-indole benzyl acetate.

EXAMPLE 2

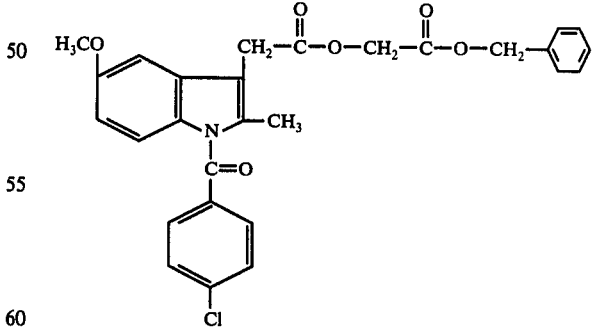

(a) 300 g (0.82 mol) of (5-methoxy-2-methyl-3-indoleacetoxy)-benzyl acetate are dissolved in 4000 ml of absolute 1,2-dichlorobenzene, an oxygen-free nitrogen stream is conducted through the solution and heating takes place to an internal temperature of 160° C. Within 20 to 30 minutes, 286 g (1.63 mol) of p-chlorobenzoyl chloride are introduced dropwise into the solution and the latter is boiled for 23 hours at an internal temperature of 180°–183° C. The degree of the conversion is determined titrimetrically by introducing the liberated hydrogen chloride into the calculated quantity of sodium hydroxide solution. After cooling the solution, solvent and excess acid chloride are distilled off at 50° C/0.1 mm Hg and the oily residue is dissolved in 1500 ml of diethylether. From the solution, cooled to −15° C, the formed [1-(p-chlorobenzoyl)-5-methoxy-2-methyl-3-indoleacetoxy]-benzyl acetate crystallises in the form of small light yellow needles, these being freed from adhering acid chloride by digestion in 1000 ml of diisopropylether. Crude yield 358 g (87% of the theoretical; melting point 89°–91° C), while after recrystallisation from ethyl acetate/diisopropylether, there are obtained 322 g (78% of the theoretical) with a melting point of 94°–95° C.

(b) distilled white spirit ("Kristallöl 60" of SHELL, boiling range 194°–220° C) is poured onto 6 g (0.0164 mol) of (5-methoxy-2-methyl-3-indoleacetoxy)-benzyl acetate while passing through oxygen-free nitrogen and stirring, and heated to boiling point (internal temperature 194° C) and then 4.28 g (0.0246 mol) of p-chlorobenzoyl chloride are added within 10 minutes. After boiling for 9¾ hours, the bath is slowly cooled under nitrogen while stirring, an oil starting to separate out at about 130° C. Diethylether is added to the cooled batch and stirring is continued until crystallisation takes place. The yield of the [1-(p-chlorobenzoyl)-5-methoxy-2-methyl-3-indoleactoxy]-benzyl acetate obtained amounts to 6.2 g (75% of the theoretical) after recrystallisation as under (a).

(c) Under the conditions described in Example 2(a), there are formed from 183.7 g (0.5 mol) of (5-methoxy-2-methyl-3-indoleacetoxy)-benzyl acetate in 2000 ml of absolute 2,4-dichlorotoluene and 175 g (1.0 mol) of p-chlorobenzoyl chloride, after boiling for 10 hours (internal temperature 198°–200° C), 190 g (75% of the theoretical) of [1-(p-chlorobenzoyl)-5-methoxy-2-methyl-3-indoleacetoxy]-benzyl acetate with the melting point of 95° C.

EXAMPLE 3

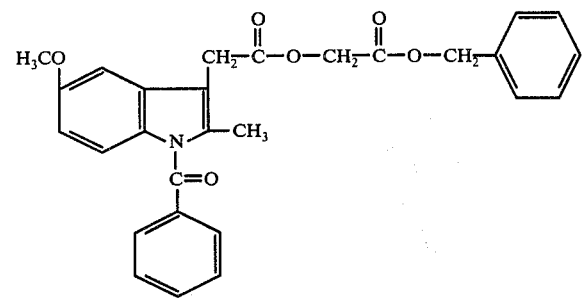

Using conditions analogous to those used in Examples 1 and 2, there are obtained from 10.0 g (0.0274 mol) of (5-methoxy-2-methyl-3-indoleacetoxy)-benzyl acetate and 7.7 g (0.0548 mol) of benzoyl chloride, after boiling for 25 hours under a nitrogen atmosphere in 130 ml of 1,2-dichlorobenzene and working up as described, 7.35 g (57% of theoretical) of (1-benzoyl-5-methoxy-2-methyl-3-indoleacetoxy)-benzyl acetate, melting at 95° C.

EXAMPLE 4

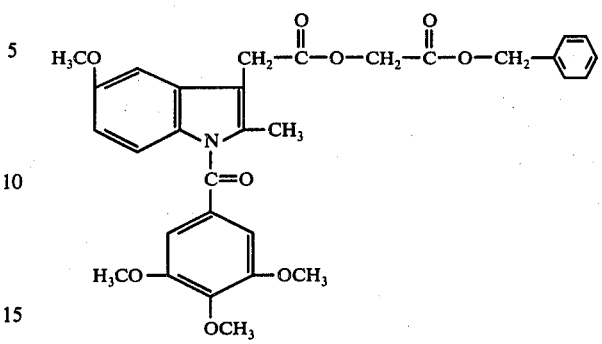

Using conditions analogous to those used in Examples 1 and 2, there are obtained 8.3 g (54% of the theoretical) of [5-methoxy-2-methyl-1-(3,4,5-trimethoxybenzoyl)-3-indoleacetoxy]-benzyl acetate from 10 g (0,0274 mol) of (5-methoxy-2-methyl-3-indole-acetoxy)-benzyl acetate and 12,6 g (0.0548 mol) of 3,4,5-trimethoxybenzoyl chloride after boiling for 13 hours in 130 ml of 1,2-dichlorobenzene and working up.

EXAMPLE 5

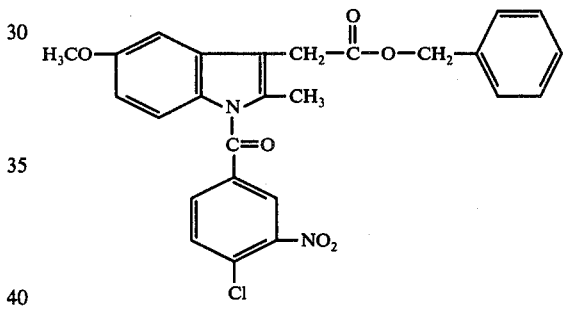

Under the conditions described in Examples 1 and 2, from 6.0 g (0.0194 mol) of 5-methoxy-2-methyl-3-indole benzyl acetate and 6.18 g (0.0291 mol) of 4-chloro-3-nitrobenzoyl chloride, by boiling for 2 hours in 400 ml of white spirit (b.p. 190°–220° C), followed by purification from chloroform on silica gel and elution with cyclohexane/ethyl acetate (3:1), there are obtained 4.6 g (48% of the theoretical) of 1-(4-chloro-3-nitrobenzoyl)-5-methoxy-2-methyl-3-indole benzyl acetate of melting point 85°–87° C.

We claim:

1. Process for the production of a compound of the formula

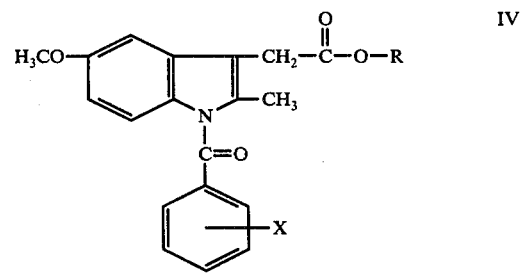

IV in which R stands for a benzyl radical or the radical

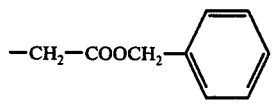

and X is hydrogen or represents one or more of halogen, methoxy, nitro, and trifluormethyl, wherein a compound of the formula

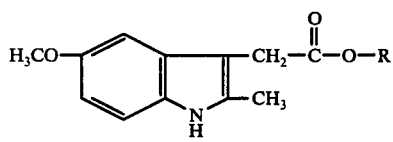 VII is condensed with a compound of the formula

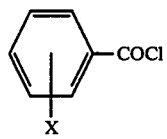 VIII in which R and X have the meaning indicated, at temperatures of at least 100° C in an inert solvent as reaction medium, with formation of free HCl.

2. Process according to claim 1, wherein each X is a hydrogen, halogen, methoxy, nitro or trifluormethyl group.

3. Process according to claim 1, wherein compound VIII is benzoyl chloride, p-chlorobenzoyl chloride, 3,4,5-trimethoxybenzoyl chloride and 4-chloro-3-nitrobenzoyl chloride.

4. Process according to claim 1, wherein compound VIII is p-chlorobenzoylchloride.

5. Process according to claim 1, wherein compound VIII is benzoyl chloride.

6. Process according to claim 1, wherein compound VIII is trimethoxybenzoyl chloride.

7. Process according to claim 1, wherein compound VIII 4-chloro-3-nitrobenzoylchloride.

8. Process according to claim 1, wherein the condensation is conducted in the absence of oxygen.

9. Process according to claim 8, wherein a stream of inert gas is passed through the reaction medium.

10. Process according to claim 1, wherein the temperature is 100° to 220° C.

11. Process according to claim 1, wherein the temperature is 170°–210° C.

12. Process according to claim 1, wherein the condensation is conducted in the absence of moisture.

13. Process according to claim 1, wherein the condensation is conducted in the absence of light.

* * * * *

UNITED STATES PATENT AND TRADEMARK OFFICE
CERTIFICATE OF CORRECTION

PATENT NO. : 4,104,278
DATED : August 1, 1978
INVENTOR(S) : Karl-Heinz Boltze, Otfried Brendler, and Peter-Rudolf Seidel It is certified that error appears in the above-identified patent and that said Letters Patent are hereby corrected as shown below:

Abstract, 6 th line from the bottom, change "on" to --in--;

column 8, line 26, change "If" to --It--;

column 9, line 64, change "95°" to --93°--;

column 10, line 42, change "of" (first occurrence to --and--;

claim 6, line 2, after "is" insert --3,4,5- --;

claim 7, line 2, after "VIII" insert --is--.

Signed and Sealed this

Twenty-seventh Day of March 1979

[SEAL]

Attest:

RUTH C. MASON
Attesting Officer

DONALD W. BANNER
Commissioner of Patents and Trademarks